(12) United States Patent
Trupke et al.

(10) Patent No.: US 10,241,051 B2
(45) Date of Patent: *Mar. 26, 2019

(54) METHODS FOR INSPECTING SEMICONDUCTOR WAFERS

(71) Applicant: BT IMAGING PTY LTD., Redfern, New South Wales (AU)

(72) Inventors: Thorsten Trupke, Coogee (AU); Juergen Weber, Coogee (AU)

(73) Assignee: BT IMAGING PTY LTD, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/851,993

(22) Filed: Dec. 22, 2017

(65) Prior Publication Data

US 2018/0136130 A1 May 17, 2018

Related U.S. Application Data

(63) Continuation of application No. 14/411,915, filed as application No. PCT/AU2013/000731 on Jul. 5, 2013, now Pat. No. 9,885,662.

(30) Foreign Application Priority Data

Jul. 6, 2012 (AU) ................................ 2012902891

(51) Int. Cl.
*G01J 3/00* (2006.01)
*G01N 21/64* (2006.01)
(Continued)

(52) U.S. Cl.
CPC ..... *G01N 21/6489* (2013.01); *G01N 21/6456* (2013.01); *G01N 21/9501* (2013.01);
(Continued)

(58) Field of Classification Search
CPC ........... G01N 21/9501; G01N 21/6489; G01N 2021/8887
(Continued)

(56) References Cited

U.S. PATENT DOCUMENTS 7,525,649 B1  4/2009  Leong et al.
8,064,054 B2  11/2011  Trupke
(Continued)

FOREIGN PATENT DOCUMENTS

DE   102004014099 A1   10/2004
JP      200912206 A     6/2009
(Continued)

OTHER PUBLICATIONS

Trupke et al 'Progress with Luminescence Imaging for the Characterisation of Silicon Wafers and Solar Cells', p. 22-31, 22nd European Photovoltaic Solar Energy Conference, Sep. 3-7, 2007.
(Continued)

*Primary Examiner* — Hoa Q Pham
(74) *Attorney, Agent, or Firm* — Mattingly & Malur, PC

(57) ABSTRACT

Methods and systems are presented for analyzing semiconductor materials as they progress along a production line, using photoluminescence images acquired using line-scanning techniques. The photoluminescence images can be analyzed to obtain spatially resolved information on one or more properties of said material, such as lateral charge carrier transport, defects and the presence of cracks. In one preferred embodiment the methods and systems are used to obtain series resistance images of silicon photovoltaic cells without making electrical contact with the sample cell.

20 Claims, 9 Drawing Sheets

(51) Int. Cl.
*G01N 21/95* (2006.01)
*G01R 31/265* (2006.01)

(52) U.S. Cl.
CPC ... *G01R 31/2656* (2013.01); *G01N 2021/646* (2013.01); *G01N 2201/062* (2013.01)

(58) Field of Classification Search
USPC .............................. 356/300, 301; 250/458.1
See application file for complete search history.

(56) References Cited

U.S. PATENT DOCUMENTS

| | | | |
|---|---|---|---|
| 8,710,860 | B2 | 4/2014 | Trupke |
| 9,035,267 | B2 | 5/2015 | Maxwell |
| 9,482,625 | B2 | 11/2016 | Trupke |
| 9,885,662 | B2 * | 2/2018 | Trupke ............... G01N 21/6489 |
| 2004/0029390 | A1 | 2/2004 | Yamamoto et al. |
| 2005/0174583 | A1 * | 8/2005 | Chalmers ........... G01B 11/0625 356/630 |
| 2006/0262296 | A1 | 11/2006 | Higgs |
| 2009/0051914 | A1 | 2/2009 | Trupke et al. |
| 2009/0206287 | A1 | 8/2009 | Trupke et al. |
| 2009/0296075 | A1 | 12/2009 | Hu |
| 2010/0025588 | A1 | 2/2010 | Trupke et al. |
| 2011/0012636 | A1 | 1/2011 | Carstensen et al. |
| 2011/0025839 | A1 | 2/2011 | Trupke et al. |
| 2011/0188733 | A1 | 8/2011 | Bardos et al. |
| 2012/0113415 | A1 | 5/2012 | Haunschild et al. |
| 2012/0142125 | A1 | 6/2012 | Trupke et al. |
| 2012/0181452 | A1 | 7/2012 | Trupke |
| 2012/0203494 | A1 | 8/2012 | Haunschild et al. |
| 2013/0043405 | A1 | 2/2013 | Maxwell et al. |
| 2013/0062536 | A1 | 3/2013 | Bardos et al. |
| 2014/0039820 | A1 | 2/2014 | Trupke et al. |
| 2014/0210995 | A1 | 7/2014 | Abe |
| 2016/0322934 | A1 | 11/2016 | Nos Aguila |

FOREIGN PATENT DOCUMENTS

| | | |
|---|---|---|
| WO | 2009129575 A1 | 10/2009 |
| WO | 2010130013 A1 | 11/2010 |

OTHER PUBLICATIONS

Trupke et al 'Spatially Resolved Series Resistance of Silicon Solar Cells Obtained from Luminescence Imaging', Applied Physics Letters val 90, 093506, Feb. 28, 2007.
Search Report issued in respect of counterpart Chinese application No. 201380035976.6 dated Aug. 18, 2016.

* cited by examiner

METHODS FOR INSPECTING SEMICONDUCTOR WAFERS

FIELD OF THE INVENTION

The present invention relates to methods and systems for inspecting semiconductor wafers, and silicon wafers in particular, using spatially resolved photoluminescence techniques. The invention has been developed primarily for inspection of photovoltaic cells and cell precursors and will be described hereinafter with reference to this application. However it will be appreciated that the invention is not limited to this particular field of use.

RELATED APPLICATIONS

The present application claims priority from Australian provisional patent application No 2012902891, filed on 6 Jul. 2012, the contents of which are incorporated herein by reference.

BACKGROUND OF THE INVENTION

Any discussion of the prior art throughout this specification should in no way be considered as an admission that such prior art is widely known or forms part of the common general knowledge in the field.

Photoluminescence (PL) imaging, performed for example using apparatus and methods disclosed in published PCT patent application No WO 2007/041758 A1 entitled 'Method and System for Inspecting Indirect Bandgap Semiconductor Structure' and incorporated herein by reference, has been shown to be of value for characterising silicon materials and devices, and silicon wafer-based photovoltaic (PV) cells in particular. As shown schematically in FIG. 1, photoluminescence 2 generated from a sample of a semiconductor material 4 with broad area photo-excitation from a source 6 of above-bandgap light 8 can be imaged with an image capture device 10 such as a camera or CCD array via collection optics 12, with the system preferably including homogenisation optics 14 to improve the uniformity of the broad area excitation and a long-pass filter 16 in front of the camera to block stray excitation light. The system may also include one or more filters 18 to select the wavelength range of the photo-excitation. With relatively thin samples and prior to metallisation of the rear surface of a PV cell, it is also possible to have the light source 6 and camera 10 on opposite sides of the sample 4 as shown in FIG. 2, in which case the sample itself can serve as a long-pass filter. However a long-pass filter 16 may still be required if a significant amount of stray excitation light, reflected for example off other components, is reaching the camera. Either way, one or more PL images can be acquired from a sample and analysed with a computer 20 using techniques disclosed for example in published PCT patent application Nos WO 2008/014537 A1, WO 2009/026661 A1 and WO 2009/121133 A1 to obtain information on average or spatially resolved values of a number of sample properties including minority carrier diffusion length, minority carrier lifetime, dislocation defects, impurities and shunts, amongst others, or on the incidence or growth of cracks. Importantly for fragile samples such as silicon wafers, the PL imaging technique is non-contact.

Early commercial systems were designed for laboratory use where total measurement times of order 10 s are acceptable, while more recent innovations have led to line-scanning systems where wafers can be illuminated and imaged without interrupting their motion along a production line. As illustrated schematically in side view in FIG. 3, a line-scanning system typically includes beam shaping optics 22 to direct the excitation light 8 onto a sample of a semiconductor material 4, and collection optics 12 to image the emitted photoluminescence 2 onto an image capture device 24 such as a line camera, as well as various other components (homogenisation optics 14, long pass filter 16, excitation filter 18 and computer 20) as required, similar to the FIG. 1 system. The sample is moved through the measurement zone on transport belts 26 or rollers or the like, from left to right in this case as indicated by the arrow 28, so that the illuminated portion 30 and imaged portion 32 are scanned across the sample, and the line camera interrogated with an interrogation module (which may be part of or under the control of the computer 20) to build up a PL image of a substantial area of the sample. The illumination and imaging subsystems may for example be configured such that the total scanned area (i.e. the 'substantial area') corresponds to 10%, 20%, 30%, 40%, 50%, 60%, 70%, 80%, 90% or 100% of one surface of the sample. Preferably the illumination and imaging subsystems are configured such that the illuminated and imaged portions 30, 32 span the sample 4 as shown in FIG. 3A, enabling inspection of the entire area of one surface of the sample. The illuminated and imaged portions 30, 32 are typically oriented to be more or less perpendicular to the direction of motion 28, as shown in FIG. 3A.

It is also known in the art to use a time delay integration (TDI) camera instead of a line camera as the image capture device for detecting photoluminescence in a line-scanning system. A TDI camera can be thought of as an integrated array of line cameras, e.g. 96 or 128 lines of 1024, 2048, 4096 or 8192 pixels on a single chip, typically using the same silicon CCD technology as in conventional line or area cameras. TDI cameras are well suited for acquiring images of a moving sample, with the direction of movement perpendicular to the pixel lines; as the sample is moved the charge from the detected signal is transferred to the next pixel line and accumulated, with the charge transport and sample motion synchronised. Consequently, a TDI camera with N pixel lines measures the signal from a given portion of a sample N times, improving the signal-to-noise ratio by a factor of $\sqrt{N}$ to N, depending on the dominant noise source, compared to a line camera for the same total measurement time. Similar to the configuration shown in FIG. 2, line-scanning systems can be designed with the light source and image capture device on opposite sides of the sample.

Localised regions of high series resistance (i.e. series resistance problems) are a common mode of PV cell failure or undesirably low efficiency, typically caused by defects that impede the transport of charge carriers. Such defects may for example include breaks in the metal contact structure, high contact resistance between the metal fingers or the rear contact and the respective silicon surface, and cracks in the silicon. Several luminescence-based techniques have been proposed, for example in published US patent application Nos 2009/0206287 A1, 2011/0012636 A1 and 2012/0113415 A1, for acquiring so-called series resistance images of PV cells or cell precursors, where local regions of excessive series resistance are identified via areas of higher or lower luminescence intensity. However these techniques require the acquisition of two or more luminescence images, or require making electrical contact to the cell, or both, and are not ideally suited to the rapid inspection of PV cells exiting a production line that currently may operate at up to 1800 or even 3600 wafers per hour.

SUMMARY OF THE INVENTION

It is an object of the present invention to overcome or ameliorate at least one of the disadvantages of the prior art, or to provide a useful alternative. It is an object of the present invention in a preferred form to provide improved methods for characterising silicon wafers or partially or fully fabricated photovoltaic cells. It is an object of the present invention in another preferred form to provide improved methods for acquiring series resistance images of photovoltaic cells.

In accordance with a first aspect of the present invention there is provided a method for analysing a semiconductor material comprising an emitter and a base, said method comprising the steps of:

illuminating a first portion of said material with a first illumination from a light source suitable for generating a photoluminescence response from said material;

detecting photoluminescence emitted from a second portion of said material with an image capture device, wherein said first and second portions are at least partially overlapping;

scanning said first and second portions across a substantial area of said material; and interrogating said image capture device to acquire a first image of photoluminescence emitted from said substantial area, wherein the intensity of said first illumination is selected such that there is a significant lateral flow of photo-generated charge carriers out of said first portion.

In accordance with a second aspect of the present invention there is provided a method for analysing a semiconductor material comprising an emitter and a base, said method comprising the steps of:

illuminating a first portion of said material with a first illumination from a light source suitable for generating a photoluminescence response from said material;

detecting photoluminescence emitted from a second portion of said material with an image capture device, wherein said first and second portions are not overlapping;

scanning said first and second portions across a substantial area of said material; and interrogating said image capture device to acquire a first image of photoluminescence emitted from said substantial area, wherein the intensity of said first illumination is selected such that there is a significant lateral flow of photo-generated charge carriers out of said first portion.

The methods of the first and second aspects share a number of preferments.

Preferably, the methods further comprise the step of interpreting the first image to identify defects that impede carrier transport in the substantial area. The methods are preferably applied to a semiconductor material selected from the group consisting of: a photovoltaic cell; a partially metallised photovoltaic cell precursor; a photovoltaic cell precursor having an emitter layer on a base; and a photovoltaic cell precursor having a selective emitter layer on a base.

The intensity of the first illumination is preferably selected such that the lateral flow rate of photo-generated charge carriers out of the first portion is at least 10%, more preferably at least 50%, and most preferably at least 80% of the photo-generation rate. In preferred embodiments the scanning step comprises moving the material relative to the light source and the image capture device.

Preferably, the methods further comprise the step of acquiring a second image of photoluminescence emitted from the substantial area, wherein the photoluminescence of the second image is generated with illumination conditions selected such that there is a reduced lateral flow of photo-generated charge carriers compared to the lateral flow induced by the first illumination. More preferably, the illumination conditions are selected such that there is substantially no lateral flow of photo-generated charge carriers. In certain embodiments the illumination conditions comprise simultaneous illumination of the substantial area with a substantially uniform illumination intensity. In alternative embodiments the illumination conditions comprise illumination of a third portion of the material with an illumination intensity selected such that the lateral flow of photo-generated charge carriers out of the third portion is less than would occur under the first illumination, and wherein an image capture device detects photoluminescence emitted from a fourth portion of the material, wherein the fourth portion is at least partially overlapping with the third portion. In preferred embodiments the methods further comprise the step of comparing the first and second images. Preferably, the image comparison comprises calculating pixel-by-pixel intensity ratios from the first and second images.

In preferred embodiments the substantial area corresponds to an entire surface of the semiconductor material.

In accordance with a third aspect of the present invention there is provided a system for analysing a semiconductor material comprising an emitter and a base, said system comprising:

a light source adapted to illuminate a first portion of said material with a first illumination suitable for generating a photoluminescence response from said material;

an image capture device adapted to detect photoluminescence emitted from a second portion of said material, wherein said first and second portions are at least partially overlapping;

a mechanism for scanning said first and second portions across a substantial area of said material; and an interrogation module for interrogating said image capture device to acquire a first image of photoluminescence emitted from said substantial area, wherein the intensity of said first illumination is selected such that there is a significant lateral flow of photo-generated charge carriers out of said first portion.

In accordance with a fourth aspect of the present invention there is provided a system for analysing a semiconductor material comprising an emitter and a base, said system comprising:

a light source adapted to illuminate a first portion of said material with a first illumination suitable for generating a photoluminescence response from said material;

an image capture device adapted to detect photoluminescence emitted from a second portion of said material, wherein said first and second portions are not overlapping;

a mechanism for scanning said first and second portions across a substantial area of said material; and an interrogation module for interrogating said image capture device to acquire a first image of photoluminescence emitted from said substantial area, wherein the intensity of said first illumination is selected such that there is a significant lateral flow of photo-generated charge carriers out of said first portion.

The systems of the third and fourth aspects share a number of preferments.

The systems preferably comprise a processor adapted to interpret the first image to identify defects that impede carrier transport in the substantial area.

The intensity of the first illumination is preferably selected such that the lateral flow rate of photo-generated charge carriers out of the first portion is at least 10%, more preferably at least 50%, and most preferably at least 80% of the photo-generation rate.

In preferred embodiments the scanning mechanism comprises a mechanism for moving the semiconductor material relative to the light source and the image capture device.

Preferably, the systems further comprise apparatus for acquiring a second image of photoluminescence emitted from the substantial area, wherein the photoluminescence of the second image is generated with illumination conditions selected such that there is reduced lateral flow of photo-generated charge carriers compared to the lateral flow induced by the first illumination. More preferably, the illumination conditions are selected such that there is substantially no lateral flow of photo-generated charge carriers. In certain embodiments the apparatus for acquiring the second image comprises a second light source adapted to simultaneously illuminate the substantial area with a substantially uniform illumination intensity. In alternative embodiments the apparatus for acquiring the second image comprises: a second light source adapted to illuminate a third portion of the material with an illumination intensity selected such that the lateral flow of photo-generated charge carriers out of the third portion is less than would occur under the first illumination; and a second image capture device adapted to detect photoluminescence emitted from a fourth portion of the material, wherein the fourth portion is at least partially overlapping with the third portion.

Preferably, the systems further comprise a processor adapted to compare said first and second images. The processor is preferably adapted to calculate pixel-by-pixel intensity ratios from the first and second images.

In preferred embodiments at least one of the first or second image capture devices comprises a line camera or a time delay integration camera. In certain embodiments the pixels within at least one of the first or second image capture devices comprise silicon, InGaAs or InGaAsP. In alternative embodiments at least one of the first or second image capture devices comprises a silicon sensor in combination with an InGaAs or InGaAsP photocathode.

The substantial area preferably corresponds to an entire surface of the semiconductor material.

In accordance with a fifth aspect of the present invention there is provided a method for inspecting a semiconductor material comprising a photovoltaic cell or cell precursor having a first passivation layer formed on a first surface and a second passivation layer formed on a second surface opposing said first surface, said method comprising the steps of:
  measuring a first photoluminescence signal generated by illumination of said first surface with light suitable for generating photoluminescence from said semiconductor material;
  measuring a second photoluminescence signal generated by illumination of said second surface with light suitable for generating photoluminescence from said semiconductor material; and
  analsysing said first and second photoluminescence signals to obtain information on at least one of said first and second passivation layers.

The first and second photoluminescence signals preferably comprise first and second spatially resolved images of photoluminescence generated by illumination of the first and second surfaces respectively. Preferably, the analysing step comprises calculating one or more metrics from an intensity ratio or intensity difference between the first and second photoluminescence signals. The intensity ratio or intensity difference is preferably calculated on a pixel by pixel basis for equivalent sample areas.

In accordance with a sixth aspect of the present invention there is provided a method according to the first, second or fifth aspect, when applied in-line in a photovoltaic cell manufacturing process for quality control or process control purposes.

In accordance with a seventh aspect of the present invention there is provided a system according to the third or fourth aspect, when used in-line in a photovoltaic cell manufacturing process for quality control or process control purposes.

In accordance with an eighth aspect of the present invention there is provided an article of manufacture comprising a computer usable medium having a computer readable program code configured to implement the method according to the first, second, fifth or sixth aspect, or to operate the system according to the third, fourth or seventh aspect.

BRIEF DESCRIPTION OF THE DRAWINGS

Benefits and advantages of the present invention will become apparent to those skilled in the art to which this invention relates from the subsequent description of exemplary embodiments and the appended claims, taken in conjunction with the accompanying drawings, in which:

DETAILED DESCRIPTION

Preferred embodiments of the invention will now be described, by way of example only, with reference to the accompanying drawings.

Figure 3:
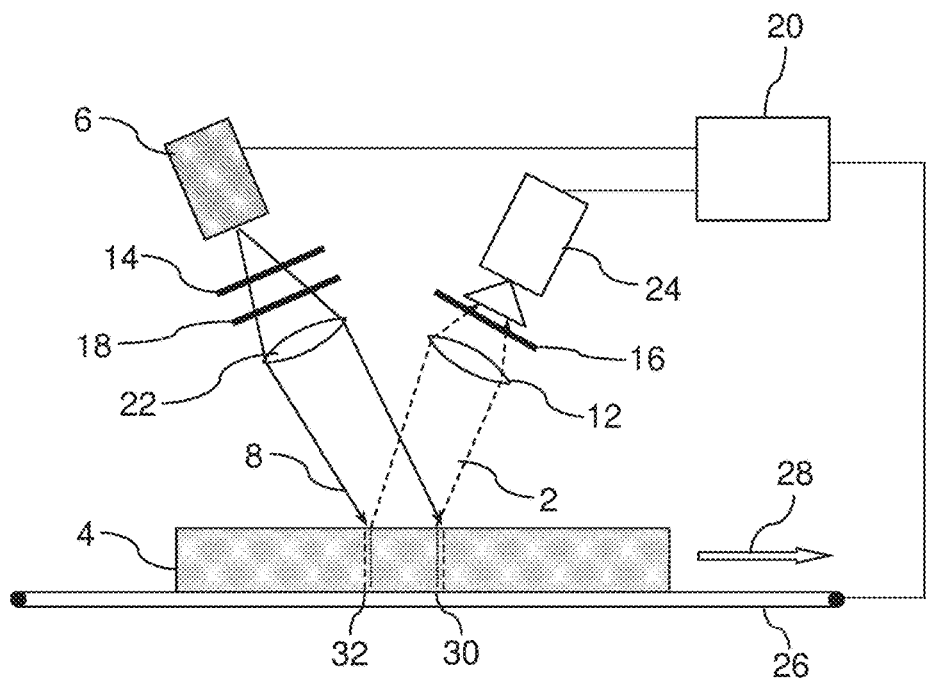
FIG. 3 illustrates in schematic side view a line-scanning system for PL imaging of a semiconductor sample.

While FIG. 3 shows in schematic form a possible configuration of a line-scanning PL imaging system, a number of design aspects need to be considered to produce a system that can actually be used for routine in-line inspection of semiconductor samples such as silicon wafers on a photovoltaic cell line, whether at the incoming wafer stage (e.g. for sorting or grading purposes) or at one or more later stages in the cell manufacture process.

Firstly, it will be evident that line-scanning systems require the illuminated and imaged portions to be scanned across the sample, for example by moving the sample 4 relative to the light source 6 and image capture device 24. For small samples such as PV cells and wafers it is generally easiest to have the light source and image capture device stationary and move the sample on transport belts or rollers or the like, as shown in FIG. 3. On the other hand for bulky samples such as silicon bricks (from which wafers are to be sawn) it may be more convenient to move the light source and image capture device, for example on rails, along a stationary sample. Other variations are also possible. For example one could hold the sample stationary, sweep the illuminated portion 30 across the sample, e.g. using a motorised mirror or shadow mask, and capture the photoluminescence with an area-imaging camera or with a combination of a line camera and a motorised mirror.

Turning now to the illuminated 30 and imaged 32 portions, while these generally need to be long enough to span the sample (e.g. at least 15.6 cm for standard photovoltaic wafers) if the entire sample is to be imaged as explained above with reference to FIG. 3A, there is considerable flexibility as to the relative widths of these portions in the scanning direction. Typically they are both in the vicinity of 0.1 to 30 mm. In certain embodiments, such as that illustrated in FIG. 3A, the illuminated and imaged portions are approximately equal in width. In other embodiments the illuminated portion is broader or narrower than the imaged portion, with both possibilities reducing the sensitivity of the system to the exact positioning of the two portions, which can be affected by variations in sample height for example. Preferably the relative widths and positions of the illuminated and imaged portions are adjustable, e.g. by adjusting the positions of the focusing or collection optics, so that they can be chosen according to various considerations. For example tighter focusing of the illumination, resulting in a narrower illuminated portion 30, increases the illumination intensity and therefore the local luminescence signal (within limits), beneficial for more rapid acquisition from low luminescence efficiency samples such as as-cut silicon wafers. On the other hand a broader illuminated portion can be useful if lower intensity illumination is required, e.g. to simulate normal PV cell operating conditions (i.e. ~1 Sun) or to enhance the lateral flow of photo-generated charge carriers for reasons explained below.

A narrower illuminated portion can be advantageous for image resolution if the image capture device has rectangular rather than square pixels. This can be explained by way of example of an InGaAs line camera having a pixel aspect ratio of 20:1 with the longer pixel sides oriented to be perpendicular to the line of pixels, and therefore parallel to the direction of motion. Because of the larger field of view per pixel in this direction, the camera inspects an area equivalent to 20 image pixels at any time. With uniform illumination of the entire field of view the image would be blurred by 20 pixels in this direction. On the other hand if the illumination is focused to a narrower line, for pre-diffusion PV samples (such bricks and as-cut wafers) at least, where lateral carrier diffusion is minimal, the spatial resolution of the system is limited only by the width of the illuminated line because the areas outside this line, while being imaged, do not contribute significantly to the measured intensity. For PV samples after emitter diffusion the situation is not as simple because the lateral flow of carriers out of the illuminated line will still result in loss of image contrast, with this effect being more severe the better the lateral conductance and the lower the illumination intensity. As discussed below, the ability to vary the illumination intensity, exploiting on occasion the lateral flow of carriers, has particular benefits for analysing silicon PV cells and cell precursors (i.e. partially fabricated cells).

Turning briefly to the excitation source 6, for eye safety considerations an incoherent source such as an LED array is preferably used, although lasers may be required for low luminescence efficiency samples because of their higher intensity and their better ability to be collimated for filtering with dielectric filters, and to be focused to a narrow line. For inspection of bulk samples such as silicon bricks where longer measurement times can be tolerated, non-laser excitation sources will generally suffice.

Figure 4:
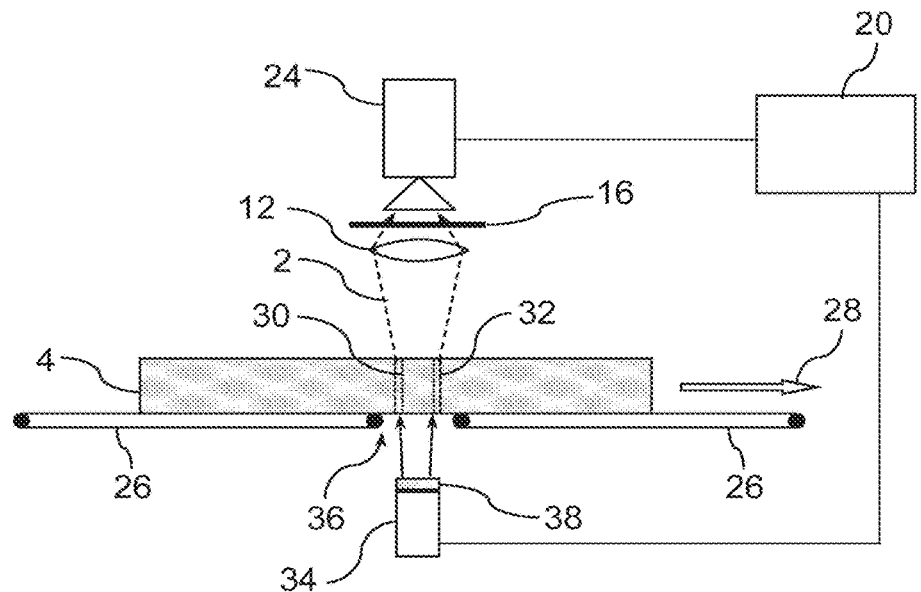
FIG. 4 illustrates in schematic side view another line-scanning system for PL imaging of a semiconductor sample.

A number of variations to the illumination system are possible. In one example embodiment shown in schematic side view in FIG. 4, an LED bar 34 is positioned to illuminate a sample 4 through a gap 36 in the transport belts 26, optionally via a diffuser 38 to improve the illumination uniformity, and the resulting luminescence 2 imaged with a line camera or a TDI camera 24. This particular configuration demonstrates a general benefit of line-scanning systems in that the excitation source can be positioned close to the sample to enhance the on-sample illumination intensity, advantageous for low luminescence efficiency samples and for simplifying the optics. Alternatively or additionally the camera can be positioned close to the sample to enhance the PL collection efficiency. While these approaches are also possible with area-imaging systems, for example using the configuration shown in FIG. 2, there are limitations for in-line applications because the transport belts will shadow parts of the sample unless they are composed of some non-standard material transparent to the illumination or luminescence. In another example embodiment the illumination intensity is further increased by providing multiple LED bars.

Apart from facilitating in-line inspection of silicon photovoltaic wafers, the Applicant has discovered that line-scanning PL imaging systems, in particular those using TDI cameras, have a number of other benefits for the characterisation of wafers and partially or fully fabricated photovoltaic cells, enhancing the measurement of several wafer or cell properties of interest to PV cell manufacturers.

In one example, line-scanning systems can provide improved image contrast compared to conventional area-imaging systems. The image contrast of PL images of silicon samples acquired with conventional Si CCD cameras is known to be significantly compromised by light spreading within the pixel array (i.e. light from one camera pixel contributing to the measured signal in another pixel), particularly with the weakly absorbed wavelengths towards the long wavelength tail of the band-to-band PL emission spectrum of silicon. Although InGaAs-based cameras don't suffer from this inter-pixel light spreading artefact because the long wavelength tail of the silicon photoluminescence is strongly absorbed by InGaAs, the image contrast is still degraded by light spreading within the sample itself. In a line-scanning system however, it turns out that because only a small fraction of a wafer (typically less than 10% of the area of one surface) is illuminated at any time, these light spreading artefacts are significantly reduced. The resulting increase in dynamic range (i.e. contrast) in PL images is particularly important for wafers and bricks as described in more detail below.

As mentioned above, line-scanning systems can be designed with image capture devices in the form of line cameras, which have a single row of pixels, or TDI cameras, which accumulate signals captured from a moving sample by multiple rows of pixels. TDI cameras are generally preferred because a lower PL signal is required to achieve a specific signal to noise ratio, enabling the use of lower illumination intensities. Apart from considerations of power consumption and eye safety, this also enables samples to be inspected at lower injection conditions, minimising or eliminating non-linear sample response, which in turn reduces the sensitivity to intensity uniformity along the illuminated line. To explain, in any luminescence imaging system the measured intensity distribution observed in an image should reflect as accurately as possible the actual local emission intensity from the sample. Ideally, a uniform quality sample with a uniform emission profile should result in an image with uniform intensity (i.e. a featureless image). In reality however images are affected by the non-uniform response of the detection system (lenses, filters, camera) and by non-uniform illumination. The combined effect of all these non-uniformities can be compensated if the individual effects are all linear, however this is the case only for PL images of as-cut wafers under true low injection conditions, i.e. where the PL intensity increases linearly with excitation light intensity. As the excitation light intensity is increased to levels that correspond to medium to high injection conditions, the PL intensity increases super-linearly and eventually quadratically with excitation light intensity, in which case accurate correction of illumination non-uniformities generally requires accurate knowledge of the doping density and the excess carrier density. However in most cases this latter information is not available, so low injection conditions are to be preferred wherever possible, subject to the sometimes opposing constraint of generating a sufficient level of luminescence.

Si-CCD camera technology is well advanced, with area, line and TDI cameras all being commercially available. Other detector technologies such as InGaAs and InGaAsP cameras, or silicon sensor arrays in combination with InGaAs or InGaAsP photocathodes, are viewed as alternatives for luminescence imaging of silicon-based PV cells and cell precursors, because unlike Si cameras they are sensitive across the entire band-to-band emission spectrum of silicon; furthermore InGaAs can also measure the so-called defect band emission from silicon around 1500 nm. TDI cameras with InGaAs or InGaAsP pixels, or silicon sensors in combination with an InGaAs or InGaAsP photocathode, would be useful alternatives to Si TDI cameras for PL-based inspection of silicon samples, but to the Applicant's knowledge are not yet commercially available. As a substitute, it is possible to use an area-imaging camera (with a rectangular or square array) instead of a TDI camera in a line-scanning system by taking multiple exposures of the sample and performing the pixel shifting retrospectively using software. This achieves a similar total exposure time as with a true TDI camera, however since every frame is associated with read noise the total noise will be substantially higher than in a TDI camera, where each line is read only once (at the end of the TDI array).

Figure 5A:
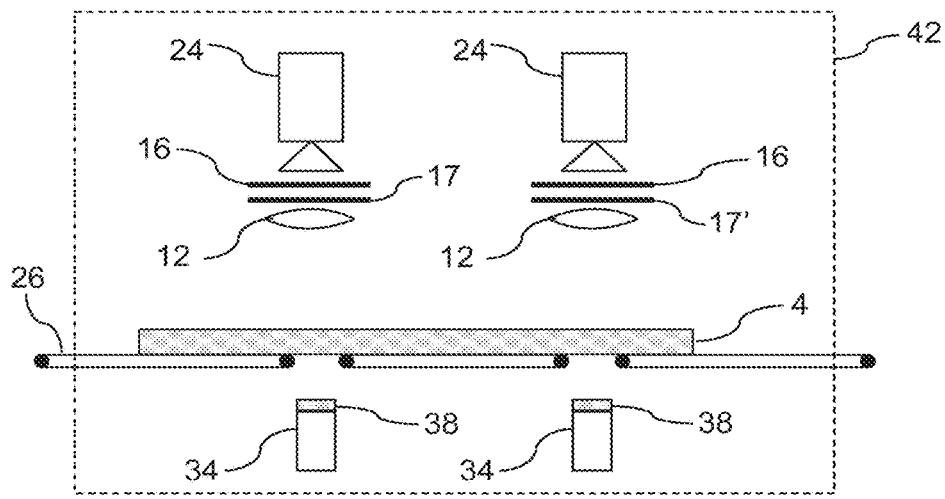
FIGS. 5(a) and 5(b) illustrate in schematic side view yet other line-scanning systems for PL imaging of a semiconductor sample.
Figure 5B:
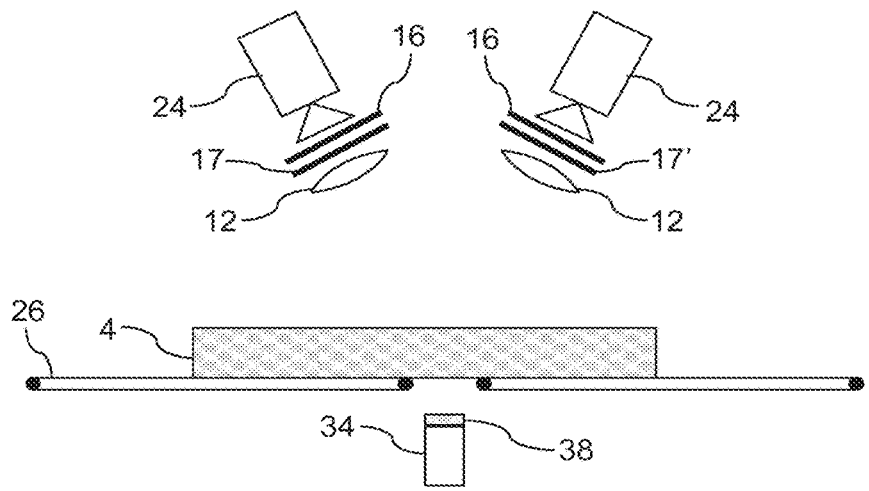

For characterising or inspecting semiconductor samples it is often beneficial to acquire two or more PL images of a sample under different conditions, which may include different excitation conditions (e.g. illumination intensity, wavelength, uniformity or area), different detection wavelengths, different basic geometry (i.e. same side or opposite side illumination/detection), or combinations thereof. In some embodiments multiple illumination and imaging subsystems are used as shown in FIG. 5(a), while in other embodiments two or more cameras 24 share a single light source 34 as shown in FIG. 5(b), noting that the cameras can be on the same side of the sample as shown, or on opposite sides. Multiple illumination and imaging systems can be housed in a common station 42 as shown in FIG. 5(a), or a sample can pass sequentially through two or more PL imaging stations. In certain embodiments different filters or filter combinations 17, 17' are used to select different detection wavelength bands, while in other embodiments two or more light sources 34 can be configured to provide different excitation wavelengths or intensities. Analyses based on combinations of PL images acquired under different conditions, e.g. pixel-by-pixel difference or ratio images, can be used to calculate material properties such as carrier lifetime, or as metrics in photovoltaic cell production. For example the intensity ratio of two PL images acquired with 1 Sun and 10 Suns illumination (~100 mW/cm$^2$ and ~1 W/cm$^2$ respectively) can be a metric. Such metrics can be used for statistical purposes, for instance within a manufacturing execution system (MES), which in turn is used to maintain the manufacturing process within a tight process window and to find and report outliers. Metrics may also be linked qualitatively or quantitatively with various material properties including background doping density, the presence and distribution of structural or atomic defects, series resistance of metallised samples and the conductivity of emitter layers or selective emitter structures, or with various process parameters including emitter diffusion and antireflection coating deposition. For example images acquired under high and low injection conditions, e.g. with high and low illumination intensities, can be compared to provide information on the background doping density in a silicon wafer.

Figure 6A:
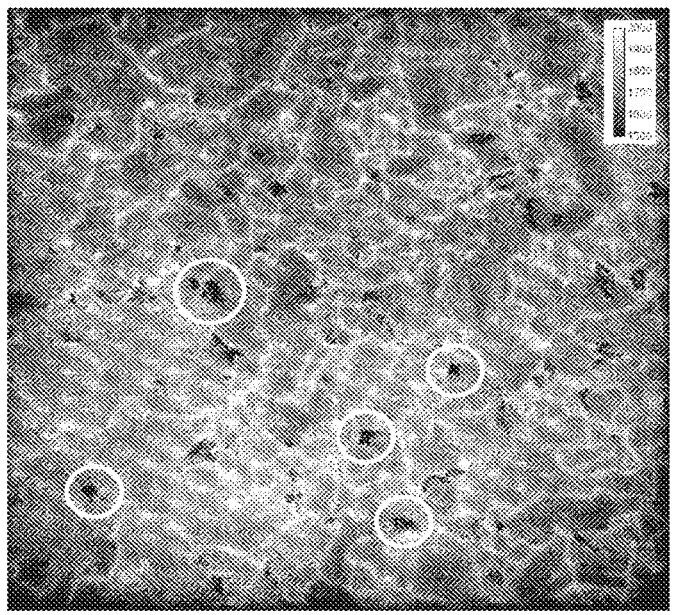
FIGS. 6(a) and 6(b) show PL images of an as-cut silicon wafer acquired using different illumination intensities.
Figure 6B:
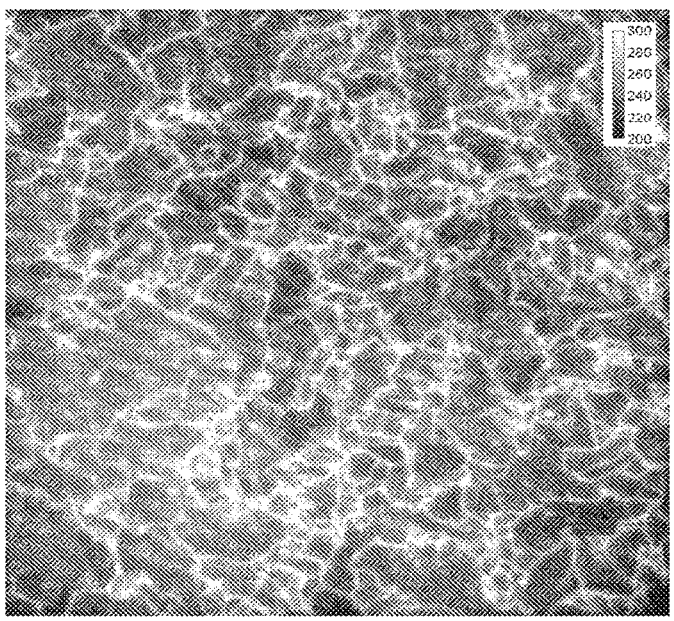

Analyses based on combinations of PL images acquired under different conditions can also be used to distinguish between different types of defects. By way of example, FIGS. 6(a) and 6(b) show PL images of a multicrystalline silicon wafer cut from the bottom portion of a brick where impurity levels are high, acquired with illumination intensities of 1 Sun (~100 mW/cm$^2$) and 20 Suns (~2 W/cm$^2$) respectively. Both images show the grain boundary structure as a network of brighter lines, with the contrast inversion typical of highly impure wafers where the gettering effect of the grain boundaries improves the quality of the immediately surrounding silicon. However there are several dislocation clusters, some of which are highlighted with circles in FIG. 6(a), that appear only in the image acquired with the lower illumination intensity. Comparison of the two images, e.g. by difference (i.e. subtraction), therefore allows dislocations to be distinguished from grain boundaries.

Referring back to FIG. 5(a), it will be appreciated that an inspection system could alternatively be constructed with an optical imaging (reflection or transmission) unit and a PL imaging unit instead of two PL imaging units, enabling comparison, e.g. by difference or ratio, of a PL image and an optical image, for example for distinguishing grain boundaries (discernible in both types of image) from dislocations (discernible in PL images only).

Figure 7A:
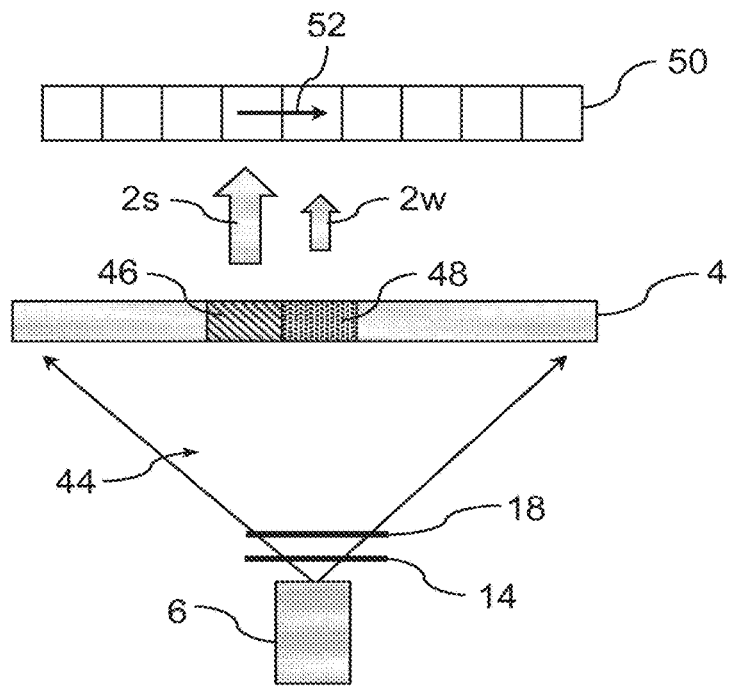
FIGS. 7(a) and 7(b) respectively illustrate the presence and absence of a light scattering artefact under broad area and line illumination regimes.
Figure 7B:
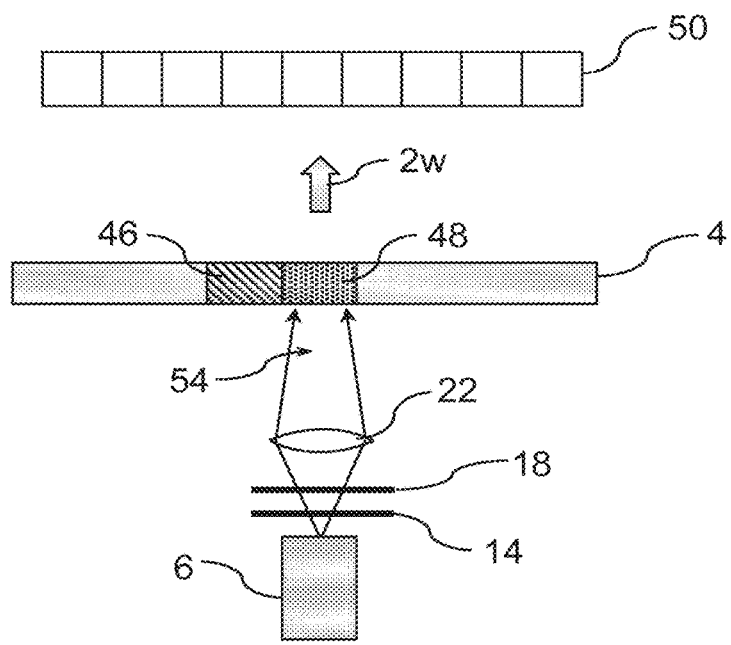

As described in published PCT patent application No WO 2011/009159 A1, the intensity ratio of two PL images acquired in different detection bands (e.g. using long pass and short pass filters) is a convenient method for measuring the bulk lifetime of silicon bricks. However as described in B. Mitchell et al 'Bulk minority carrier lifetimes and doping of silicon bricks from photoluminescence intensity ratios, Journal of Applied Physics vol 109, 083111 (2011), this method tends to overestimate the bulk lifetime in low lifetime regions, e.g. in the impurity-rich regions at the top and bottom parts of a brick. The Applicant has determined that this is an artefact arising from the use of an area CCD camera, caused by the above-described light spreading effect between the camera pixels; this effect is particularly pronounced for weakly absorbed long wavelength photons and therefore tends to affect the long wavelength PL image. The problem is greatly reduced with a line-scanning PL imaging system, since adjacent high and low lifetime regions are less likely to be excited at the same time. To explain, FIGS. 7(a) and 7(b) illustrate the respective situations with broad area and line illumination. As shown in FIG. 7(a), with broad area illumination 44 adjacent high and low lifetime regions 46, 48 of a wafer 4 are both excited, producing strong and weak PL emission $2s$, $2w$ directed to different portions of the camera pixel array 50. Long wavelength photons from the strong emission can be scattered within the camera as represented by the arrow 52 before being absorbed, thereby artificially increasing the signal detected from the low lifetime region 48. This artefact is particularly problematic in situations where a small region of lower lifetime material is surrounded by higher lifetime material. On the other hand, as shown in FIG. 7(b), with line illumination 54 the adjacent high and low lifetime regions are generally not excited simultaneously, enabling the weak PL emission $2w$ from the low lifetime region 48 to be measured in isolation.

A commercial system for measuring the bulk lifetime of silicon bricks could use either a single line camera or TDI camera with a filter wheel to take the two or three images that are required, or two or more line or TDI cameras equipped with a different filter combination and with dedicated or shared light sources 34 as shown in FIGS. 5(a) and 5(b) respectively.

Figure 1:
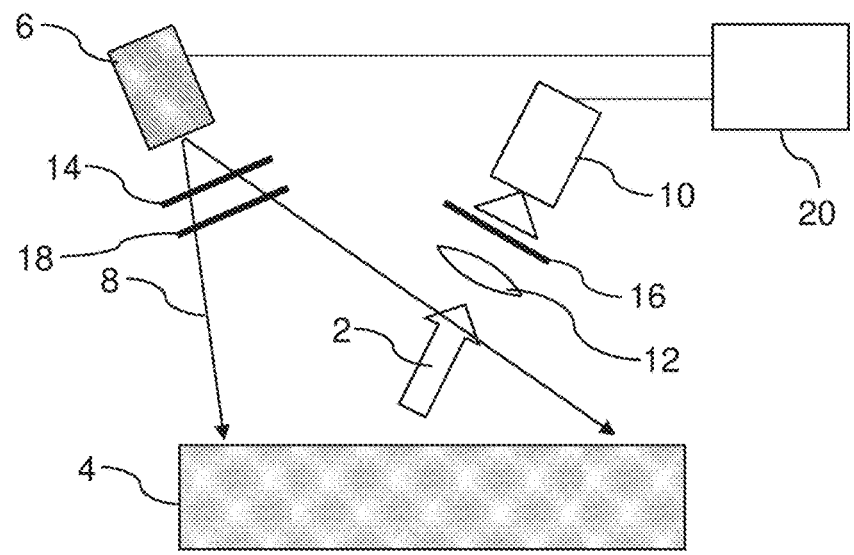
FIG. 1 illustrates in schematic side view an area-imaging system for photoluminescence (PL) imaging of a semiconductor sample.
Figure 2:
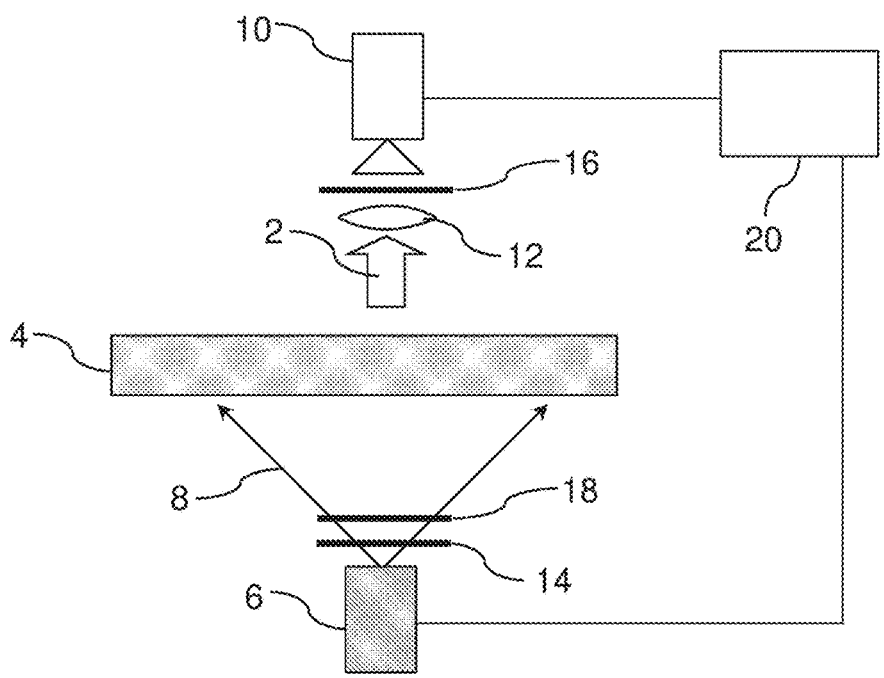
FIG. 2 illustrates in schematic side view another area-imaging system for PL imaging of a semiconductor sample.

Surface passivation is a standard process step in silicon photovoltaic cell manufacture, for enhancing the carrier lifetime and hence cell efficiency. In standard cell designs only the front surface needs to be passivated, typically by forming a silicon nitride (SiN) layer, while some newer cell designs require both surfaces to be passivated, often in different fashions. For example SiN is more suitable for passivating $n^{++}$ layers, while aluminium oxide (AlO) is more suitable for passivating $p^{++}$ layers, because of their different surface charges. PL signals measured from opposite sides of a sample, e.g. with two TDI or other line-scanning systems, or with conventional area-imaging systems as shown in FIG. 1 or 2, can provide information about absolute surface passivation or relative variations in passivation between the front and rear surfaces. In certain embodiments these signals are measured with simple photodetectors from selected portions of the front and rear surfaces, while in other embodiments they comprise spatially resolved PL images acquired from the two surfaces, e.g. using known area-imaging or line-scanning techniques. Metrics derived from these signals can be used to monitor the effectiveness of the respective passivation steps. For example in PV cell production a specific PL intensity ratio or intensity difference, which in certain embodiments is calculated on a pixel-by-pixel basis for equivalent sample areas, could be used as a metric that has to be maintained within a specific range, with drifts alerting the operator or process control system to a problem with one or other of the passivation steps. In certain embodiments two PL imaging systems are used, where in each case the light source and image capture device can be on the same or opposite sides of a sample wafer as explained previously. In other embodiments a single light source is used and two image capture devices measure the PL from the front and rear surfaces respectively.

Dielectric coatings such as passivation layers and anti-reflection coatings are well known to change the colour of wafers, and several spectral reflectance techniques are known for monitoring the thickness and refractive index of such coatings. The Applicant has realised that these coatings will also influence the wavelength range of light coupled into a wafer and of light that escapes a wafer. It follows that thickness or refractive index variations in a dielectric coating will be revealed in variations in the intensity of PL measured either with different excitation wavelengths, or different detection wavelengths, or both.

As described in published PCT application No WO 10/130013 A1, imaging of luminescence generated with a spatially non-homogeneous illumination pattern can be used to analyse PV cells or cell precursors (i.e. fully or partially fabricated PV cells) for a variety of defects that interfere with the transport of photo-generated charge carriers. As explained therein, photo-generated charge carriers that are able to be transported laterally out of an illuminated region through an emitter layer or other conductive structure can recombine radiatively to generate luminescence from a non-illuminated region. Example applications based on this principle include the detection of cracks that disrupt carrier transport through the emitter layer of a partially or fully fabricated cell or along the highly-doped lines of a selective emitter structure, and the detection of series resistance problems such as excessive localised contact resistance or metallisation breaks in a partially metallised or fully fabricated cell. It was suggested that spatially resolved conductivity or series resistance information across an entire wafer or cell could be obtained from a series of two or more luminescence images acquired with different illumination patterns, such as complementary chequerboard patterns, optionally in comparison with standard PL images, i.e. images acquired with substantially uniform broad area illumination.

As mentioned above, known luminescence-based techniques for obtaining series resistance images of PV cells require the acquisition of two or more luminescence images, or require making electrical contact to the cell, or both. The Applicant has now determined that information on defects that impede carrier transport, including series resistance images of fully or partially fabricated cells, can be obtained in a faster and more convenient fashion, and without making electrical contact, with a line-scanning PL imaging system. Instead of applying two or more static illumination patterns as suggested in WO 10/130013 A1, a non-homogeneous illumination pattern is successively applied to a sample by scanning an illuminated portion across a substantial area of the sample. Because the lateral current, i.e. the flow of photo-generated charge carriers out of the illuminated portion, equilibrates within a microsecond, i.e. very fast compared to the ~0.3 m/s line speed required to process one wafer per second (assuming wafers are on a 30 cm pitch), the sample is essentially in steady state as far as the electrical properties are concerned. This applies irrespective of whether the illumination pattern is applied statically as in WO 10/130013 A1 or dynamically (e.g. using the wafer motion) as suggested in the present invention.

Figure 8:
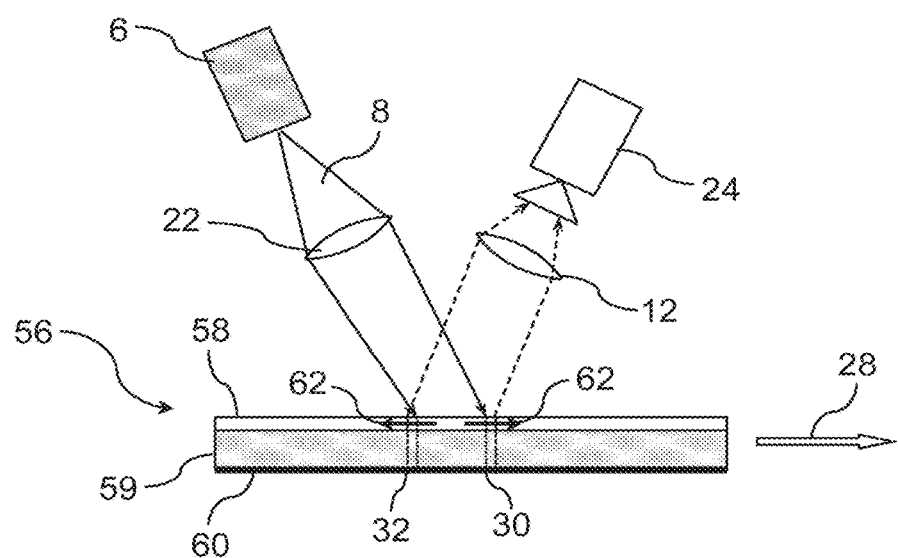
FIG. 8 illustrates in schematic side view a line-scanning PL imaging system configured for analysing lateral carrier transport in a PV cell according to an embodiment of the present invention.

In one example embodiment illustrated in side view in FIG. 8, a line-scanning PL imaging system can be used to obtain series resistance or carrier transport information across a PV cell 56 having an emitter layer 58 on a base 59 and with a metal contact pattern (typically bus bars and fingers, not shown) deposited on the emitter layer and a metal contact layer 60 on the rear surface. For clarity the illumination and imaging subsystems are simplified to show the light source 6, beam shaping optics 22, collection optics 12 and image capture device 24 only, although it will be appreciated that most or all of the other components shown in the FIG. 3 system, including the computer 20, will also be present as required. For preference the image capture device is a TDI camera. The illuminated and imaged portions 30, 32 are at least partially overlapping, and the imaged portion 32 is preferably chosen to be slightly wider than the illuminated portion 30. In certain embodiments the widths of the illuminated and imaged portions are controllable by appropriate adjustments to the beam shaping and collection optics respectively.

Importantly, the on-sample intensity of the excitation light 8 is selected such that there is a significant lateral flow of photo-generated charge carriers out of the illuminated portion 30, via the emitter layer or the metal contact pattern as shown schematically by the arrows 62, resulting in a charge carrier concentration gradient that can be measured as a spatial variation in the PL signal across the imaged portion 32. In preferred embodiments the illumination intensity is selected such the lateral flow rate of photo-generated charge carriers is at least 10%, more preferably at least 50% and most preferably at least 80% of the photo-generation rate. Specific intensities that would result in such levels of significant carrier flow depend on the nature of the sample among other factors, e.g. whether the sample only has an emitter layer or whether charge carriers can also migrate through a metal contact structure. However it is known that carrier transport through an emitter layer becomes less efficient with increasing current density, and it follows therefore that it becomes less efficient with increasing illumination intensity. With overall PV cell efficiency in mind, emitter layers are generally designed so that under 1 Sun illumination the expected lateral current densities can be transported with small transport losses and over distances comparable to the typical metal contact spacing. In the present context, lower illumination intensities will result in more efficient carrier transport but lower luminescence signals. The Applicant has determined that for standard silicon PV cells, an excitation intensity of around 1 Sun is a reasonable compromise for achieving both significant carrier flow and measurable luminescence signals.

Figure 3A:
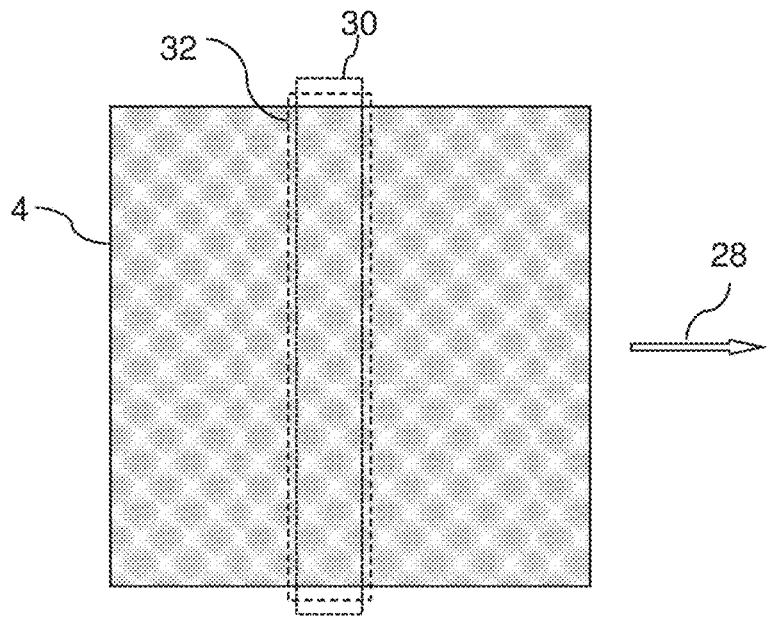
FIG. 3A shows in schematic plan view a preferred arrangement of illuminated and imaged portions for acquiring PL images of a semiconductor sample with a line-scanning system.

Turning again to FIG. 8, and as described above in relation to FIG. 3, the TDI camera 24 is interrogated by an interrogation module as the PV cell 56 moves through the illumination and imaging subsystems as shown by the arrow 28, to acquire an image of a substantial area of the cell. The substantial area may for example be 10%, 20%, 30%, 40%, 50%, 60%, 70%, 80%, 90% or 100% of one surface of the PV cell. Preferably the substantial area will correspond to an entire surface of the cell, which will typically be the case if the illuminated and imaged portions 30, 32 span the cell as shown in FIG. 3A. The interrogation module will typically be part of or controlled by a computer (not shown in FIG. 8). The important point is that with an appropriately selected illumination intensity the non-illuminated portions of the PV cell act as a sink, drawing a significant fraction of the photo-generated charge carriers out of the illuminated portion 30, so that the resulting line-scan image is equivalent to a PL image acquired under conditions of current extraction from the cell terminals. In other words the line-scanning system allows the acquisition of a current extraction PL image without having to contact the cell.

In certain embodiments the cell is also subjected to a second exposure to acquire a second image using illumination conditions that induce a reduced lateral flow of photo-generated charge carriers compared to the first exposure. Preferably the second exposure is performed using illumination conditions selected such that there is substantially no lateral flow of photo-generated charges, in which case the second exposure will result in an image essentially equivalent to a standard or open circuit PL image. The illumination conditions for the second exposure may for example comprise substantially uniform broad area illumination or high intensity scanned line illumination. An open circuit PL image can provide information on local defects (e.g. dislocations and highly impure regions) and cracks in PV cells and cell precursors, as known in the art. An open circuit PL image is also useful, in combination with PL images acquired under conditions of current injection or extraction, such as the 'current extraction' image acquired as described above using relatively low intensity illumination, for yielding spatially resolved qualitative or quantitative series resistance data. For example a comparison comprising a pixel-by-pixel intensity ratio can be used to eliminate luminescence variations caused by other factors such as background doping level variations or impurities. In preferred embodiments an open circuit PL image is acquired with a second line-scanning system as shown in FIG. 5(*a*) for example, while in other embodiments it is acquired with substantially homogeneous broad area illumination in an area-imaging system such as that shown in FIG. 1. Referring back to FIG. 8 for the case where a line-scanning system is used, on this occasion the intensity of the excitation light 8 is selected such that there is substantially no lateral flow of photo-generated charge carriers out of the illuminated portion 30. In one specific example, where the sample is a standard silicon PV cell, the on-sample intensity of the excitation light for the second exposure is selected to be 20 Suns (~2 W/cm$^2$), compared to 1 Sun for the first exposure. The specific illumination intensity is less important in embodiments where the sample is illuminated substantially homogeneously, whether the PL image is acquired with an area camera or with a TDI or line camera.

Figure 9:
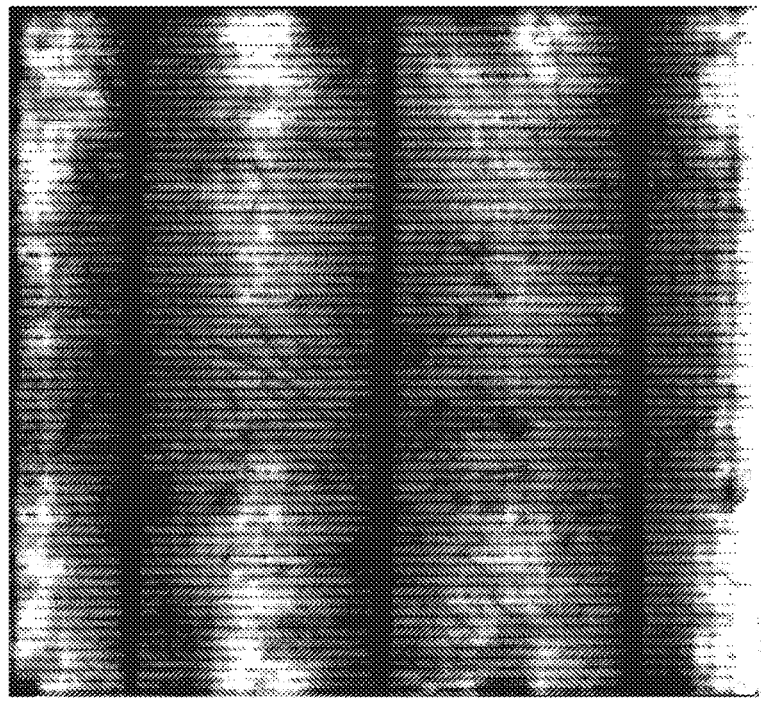
FIG. 9 shows a qualitative series resistance image of a silicon PV cell acquired according to an embodiment of the present invention.
Figure 10:
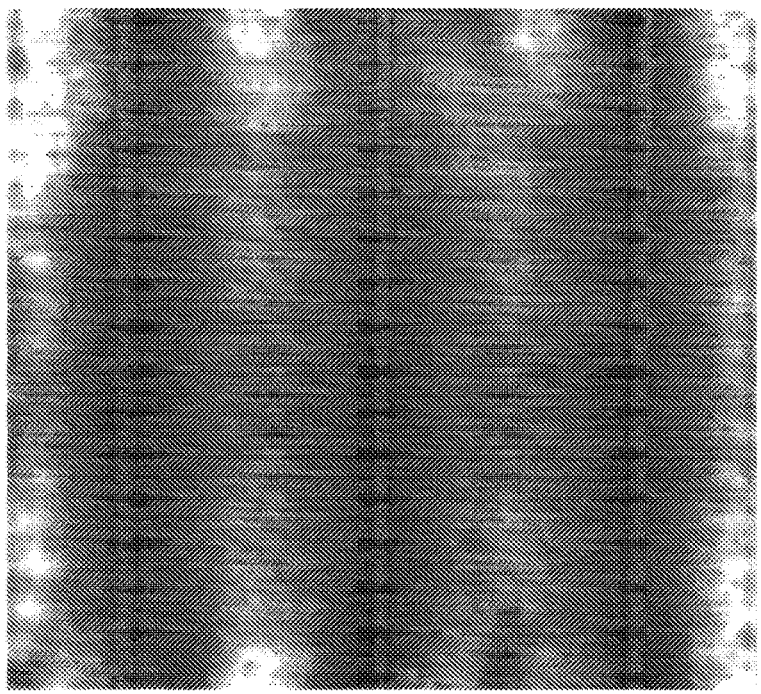
FIG. 10 shows a quantitative series resistance image of the same silicon PV cell as in FIG. 9, acquired using a known cell-contacting method.

FIG. 9 shows a PL image of a silicon PV cell acquired with a line-scanning system equipped with a Si TDI camera, where the on-sample illumination intensity was selected to be about 1 Sun to encourage lateral flow of photo-generated charge carriers. For comparison FIG. 10 shows a quantitative series resistance image taken from the same cell using a multi-image, cell-contacting method described in published PCT patent application No WO 2009/129575 A1. It will be seen that there is a strong resemblance between the two images, indicating that our simple line-scanning method, requiring only one image, is able to reveal regions with high local series resistance. In many practical instances such qualitative series resistance information is sufficient for quality control purposes, e.g. for use as a metric in PV cell production, without the additional steps necessary for producing more quantitative data, e.g. acquisition of further images such as an open circuit PL image to eliminate carrier lifetime-related luminescence variations. Local regions with particularly high series resistance are readily identified and located in qualitative series resistance images, unlike the case with standard IV testing where defective cells can be detected but the location of the defect cannot be ascertained. Qualitative images can also be useful for process control purposes, for example where specific series resistance patterns occurring repeatedly in production can be identified and used to correct a problem with a process station.

Although the line-scanning configuration shown in FIG. 8 has been described in terms of obtaining spatially resolved series resistance information on fully fabricated PV cells, it can also be used to obtain information on defects that impede charge carrier migration in a number of other types of semiconductor samples having an emitter and a base, in particular precursor cells such as post-diffusion wafers (i.e. where an emitter layer has been diffused into a base material), wafers on which a selective emitter structure has been formed, and partially metallised cells. Such defects may for example include cracks, localised regions where the diffusion process has been compromised during formation of a standard or selective emitter, and metallisation faults. Again, the information can be used for quality control purposes (e.g. rejection of defective wafers) or process control purposes (e.g. correction of an emitter diffusion process).

Figure 11A:
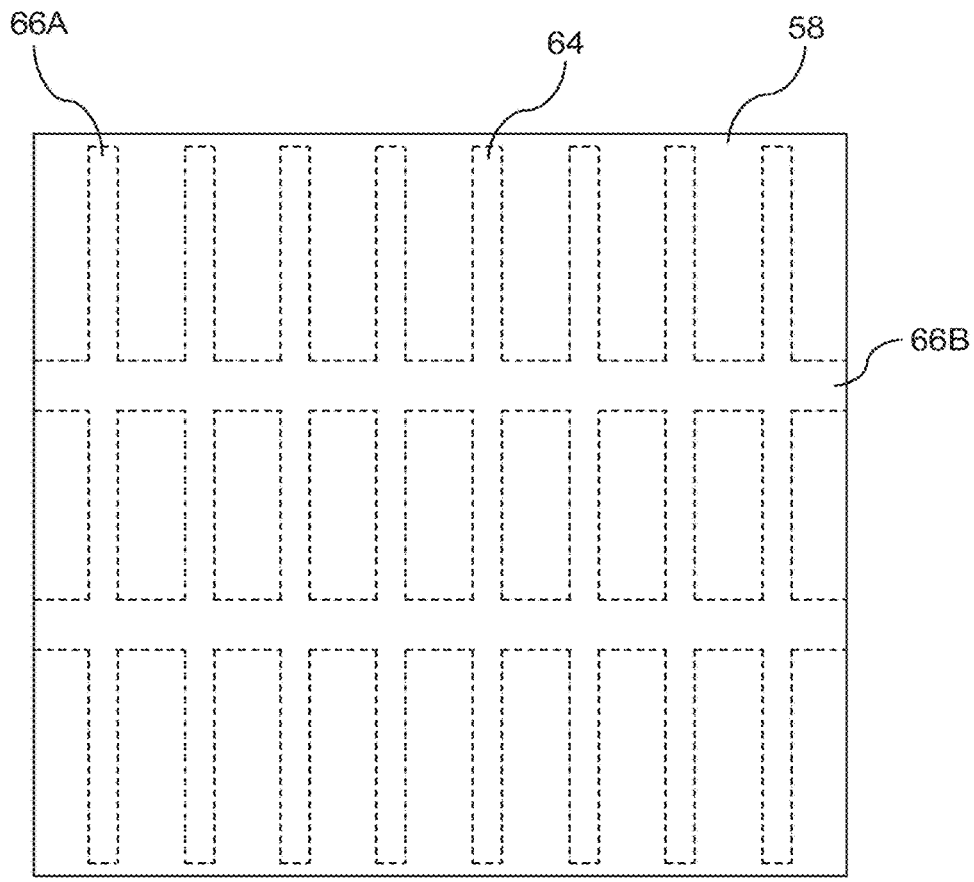
FIGS. 11(a) and 11(b) illustrate in schematic plan and side views a typical selective emitter pattern on a silicon wafer.
Figure 11B:
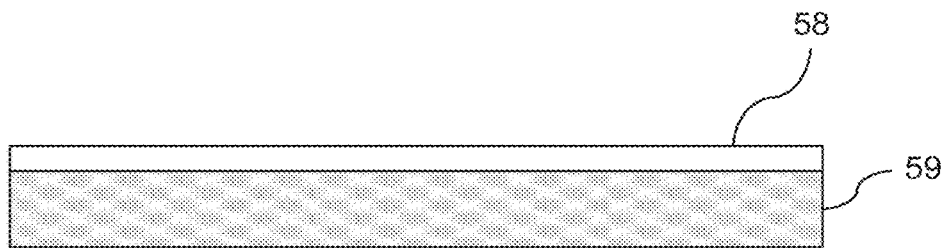

FIGS. 11(*a*) and 11(*b*) illustrate in schematic plan and side views a selective emitter structure 64 comprising a pattern of highly-doped $n^{++}$ regions within a lower doped emitter layer 58 formed on a base 59 comprising a p-type silicon wafer. A selective emitter structure typically comprises a large number of thin highly-doped strips 66A and in some cases two or three thicker highly-doped strips 66B onto which metal fingers and bus bars respectively are subsequently deposited. These $n^{++}$-doped regions typically have much higher conductivity than the surrounding emitter layer 58. In certain line-scanning embodiments a sample wafer with a selective emitter structure is oriented such that the 'finger' strips 66A are parallel to the scanning direction, while in other embodiments the sample is oriented such that the 'bus bar' strips 66B are parallel to the scanning direction. In each case the charge carrier migration stimulated by a scanned illumination line and detected via a PL image can be used to obtain a measure of the conductivity of the respective set of doped strips, and to identify defects that locally disrupt the conductivity. Additional conductivity information can be gained by tailoring the illumination intensity along the illuminated portion, e.g. by applying a quadratic or comb illumination pattern, to stimulate charge carrier migration along the doped strips perpendicular to the scanning direction.

In the line-scanning configurations illustrated in FIGS. 3 and 8 the illuminated portion 30 and the imaged portion 32 are overlapping at least partially, generally with some degree of under-filling or over-filling as described previously. The resulting luminescence image simulates a current extraction PL image. In an alternative configuration illustrated in FIG. 12(*a*), again only showing selected components of the illumination and imaging subsystems, the imaged portion 32 is displaced from the illuminated portion 30 by an optionally controllable distance such that they are not overlapping. In this case the detected luminescence signal 2 arises solely from radiative recombination of photo-generated charge carriers that have migrated 62 out of the illuminated portion, for example through an emitter layer 58 or a metal contact structure. As in the FIG. 8 configuration it is necessary for the on-sample illumination intensity to be selected such that there is a significant lateral flow of photo-generated charge carriers out of the illuminated portion 30. The illumination intensity is preferably selected such the lateral flow rate of photo-generated charge carriers is at least 10%, more preferably at least 50% and most preferably at least 80% of the photo-generation rate.

Figure 12A:
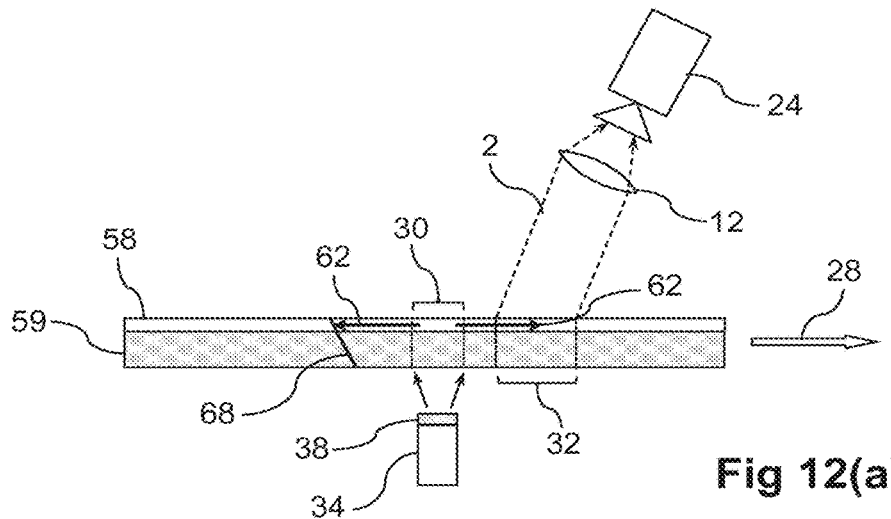
FIGS. 12(a) and 12(b) illustrate in schematic side view line-scanning PL imaging systems configured for analysing lateral carrier transport in a PV cell, according to certain embodiments of the present invention.
Figure 12B:
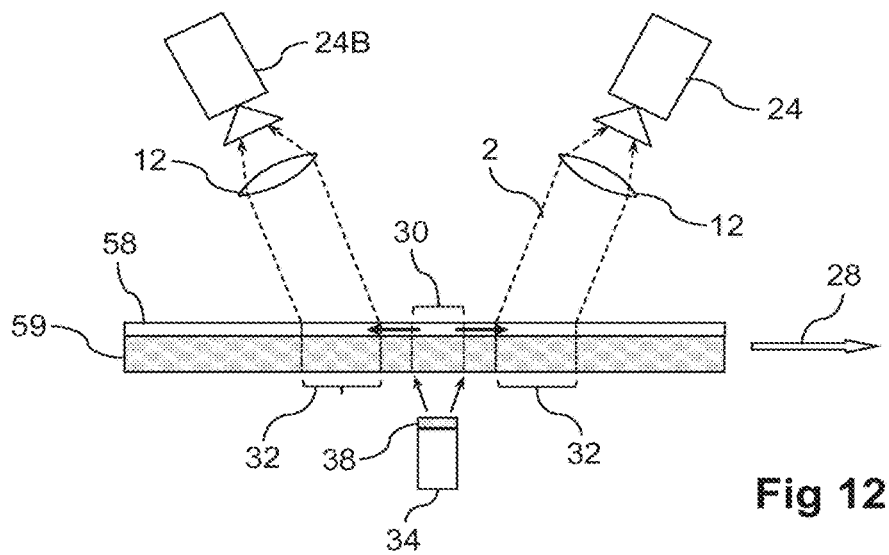

When the illuminated and imaged portions 30, 32 are not overlapping, as shown in the configurations of FIGS. 12(*a*) and 12(*b*), a luminescence image acquired as the illuminated and imaged portions are scanned across a substantial area of the sample, preferably across an entire surface of the sample, will be essentially equivalent to an electroluminescence (EL) image, i.e. an image of luminescence generated by applying a voltage to the contacts of a PV cell, with the important difference that no electrical contact is required. In one example embodiment this configuration is used to monitor the lateral conductivity of an $n^{++}$-doped emitter layer 58 diffused into a base 59 comprising a p-type silicon PV wafer; for example the location of a crack 68 that disrupts the lateral migration 62 of charge carriers will be ascertained by the appearance of a region of reduced luminescence. Preferably the apparatus includes a second line camera or TDI camera 24B positioned to acquire luminescence from the other side of the illuminated portion 30 as shown in FIG. 12(*b*), to ensure complete imaging of the sample wafer as it enters and exits the measurement zone. Again, quality control and process control applications are envisaged.

In certain embodiments the position or angle of the cameras are adjustable to control the distance between the illuminated and imaged portions 30, 32, since for samples with more efficient lateral carrier transport a luminescence signal will be observed a greater distance from the illuminated portion 30. In other embodiments the camera positions remain fixed and the illumination intensity adjusted, for example to vary the carrier transport efficiency though an emitter structure. In yet another embodiment the apparatus includes additional cameras positioned to acquire luminescence emitted from a sample wafer a greater or lesser distance from the illuminated portion. In still another embodiment an additional line or TDI camera is positioned to capture luminescence from the illuminated portion 30; as explained above an image acquired with this camera will simulate a PL image under conditions of current extraction.

The line-scanning configurations shown in 12(*a*) and 12(*b*), which essentially yield EL images, can also be used to obtain information on series resistance variations across a PV cell. Two different illumination intensities, which generate differing degrees of carrier migration, can be used to simulate images of EL generated with different voltages, which can be compared, by calculating pixel-by-pixel intensity ratios for example, to obtain quantitative series resistance data similar to known EL-based techniques, but without contacting the cell. It will be appreciated that if an additional line or TDI camera is positioned to capture luminescence from the illuminated portion 30, to obtain a current extraction image as explained previously, this additional image could also be fed into the series resistance analysis. It would also be possible to acquire an open circuit PL image, using either substantially uniform broad area illumination or high intensity line illumination as described above, for comparison with the simulated EL image.

Similar to the line-scanning configuration shown in FIG. 8, it will be appreciated that the configurations shown in FIG. 12(*a*) or 12(*b*) could be used to identify defects that impede carrier transport in a number of semiconductor samples having an emitter on a base, including photovoltaic cells, partially metallised cell precursors, and cell precursors having an emitter layer or selective emitter structure on a base.

In general the above described line-scanning systems are designed to be installed in-line at one or more positions in a PV cell manufacturing process, for example after the surface passivation or emitter diffusion steps, after one or more stages of a metallisation process, or after the cell completion, for inspecting all or at least a significant fraction of the cells being produced. Importantly, electrical contact to the cells is not required. The systems can of course be used off-line as well, for example for trouble shooting applications where a selection of precursor or completed cells are inspected. It is of course preferable for the systems to be able to inspect wafers at line speed, i.e. without slowing the wafer throughput, and if necessary measurement speed can be enhanced by sacrificing spatial resolution, e.g. with pixel binning. Although the configurations shown in FIG. 8, where the illuminated and imaged portions 30, 32 at least partially overlap, and FIGS. 12(*a*) and 12(*b*), where these portions are displaced, can both be utilised to obtain information on series resistance or carrier transport across a PV cell or cell precursor without requiring electrical contact, the former configuration is generally preferred because the luminescence signal is much higher from the illuminated portion, and because only one TDI or line camera is required to ensure complete imaging of the sample.

Although the present invention has been described with particular reference to certain preferred embodiments thereof, variations and modifications of the present invention can be effected within the spirit and scope of the following claims.

The invention claimed is:

1. A method for obtaining series resistance or carrier transport information across a semiconductor material comprising an emitter and a base, said method comprising the steps of:
    illuminating a first portion of said material with a first illumination from a light source suitable for generating a photoluminescence response from said material;
    detecting photoluminescence emitted from a second portion of said material with an image capture device, wherein said first and second portions are at least partially overlapping;
    scanning said first and second portions across a substantial area of said material, said substantial area corresponding to an entire surface of said semiconductor material; and
    interrogating said image capture device while said first and second portions are being scanned across said substantial area to acquire an image of photoluminescence emitted from said substantial area,
    wherein an intensity of said first illumination is selected such that there is a significant lateral flow of photo-generated charge carriers out of said first portion, and wherein said method further comprises the step of interpreting said image to identify defects that impede carrier transport in said substantial area.

2. A method according to claim 1, wherein said first and second portions are scanned in a scanning direction across the substantial area of said material and wherein said second portion is wider than said first portion in the scanning direction.

3. A method according to claim 1, wherein said method is applied to a semiconductor material selected from the group consisting of: a photovoltaic cell; a partially metallised photovoltaic cell precursor; a photovoltaic cell precursor having an emitter layer on a base; and a photovoltaic cell precursor having a selective emitter layer on a base.

4. A method according to claim 1, wherein the intensity of said first illumination is selected such that the lateral flow rate of photo-generated charge carriers out of said first portion is at least 10% of the photo-generation rate.

5. A method according to claim 4, wherein the intensity of said first illumination is selected such that the lateral flow rate of photo-generated charge carriers out of said first portion is at least 50% of the photo-generation rate.

6. A method according to claim 5, wherein the intensity of said first illumination is selected such that the lateral flow rate of photo-generated charge carriers out of said first portion is at least 80% of the photo-generation rate.

7. A method according to claim 1, wherein the scanning step comprises moving said material relative to said light source and said image capture device.

8. A method according to claim 1, wherein said method is applied in-line in a photovoltaic cell manufacturing process for quality control or process control purposes.

9. An article of manufacture comprising a non-transitory computer usable medium having a computer readable program code configured to implement the method according to claim 1.

10. A system for obtaining series resistance or carrier transport information across a semiconductor material comprising an emitter and a base, said system comprising:
    a light source adapted to illuminate a first portion of said material with a first illumination suitable for generating a photoluminescence response from said material;
    an image capture device adapted to detect photoluminescence emitted from a second portion of said material, wherein said first and second portions are at least partially overlapping;
    a mechanism for scanning said first and second portions across a substantial area of said material, said substantial area corresponding to an entire surface of said semiconductor material; and
    a computer programmed to interrogate said image capture device while said first and second portions are being scanned across said substantial area to acquire an image of photoluminescence emitted from said substantial area,
    wherein an intensity of said first illumination is selected such that there is a significant lateral flow of photo-generated charge carriers out of said first portion, and wherein said computer is programmed to interpret said image to identify defects that impede carrier transport in said substantial area.

11. A system according to claim 10, wherein said mechanism is configured to scan said first and second portions in a scanning direction across the substantial area of said material and wherein said second portion is wider than said first portion in the scanning direction.

12. A system according to claim 10, wherein the intensity of said first illumination is selected such that the lateral flow rate of photo-generated charge carriers out of said first portion is at least 10% of the photo-generation rate.

13. A system according to claim 12, wherein the intensity of said first illumination is selected such that the lateral flow rate of photo-generated charge carriers out of said first portion is at least 50% of the photo-generation rate.

14. A system according to claim 13, wherein the intensity of said first illumination is selected such that the lateral flow rate of photo-generated charge carriers out of said first portion is at least 80% of the photo-generation rate.

15. A system according to claim 10, wherein the scanning mechanism comprises a mechanism for moving said semiconductor material relative to said light source and said image capture device.

16. A system according to claim 10, wherein said image capture comprises a line camera or a time delay integration camera.

17. A system according to claim 10, wherein the pixels within said image capture device comprise silicon, InGaAs or InGaAsP.

18. A system according to claim 10, wherein said image capture device comprises a silicon sensor in combination with an InGaAs or InGaAsP photocathode.

19. A system according to claim 10, when used in-line in a photovoltaic cell manufacturing process for quality control or process control purposes.

20. An article of manufacture comprising a non-transitory computer usable medium having a computer readable program code configured to operate the system according to claim 10.

* * * * *